(12) United States Patent
Christy

(10) Patent No.: US 6,387,055 B1
(45) Date of Patent: May 14, 2002

(54) TACTILE SENSORY TESTING DEVICE

(76) Inventor: George Michael Christy, 2108 Raven Rd., Pleasanton, CA (US) 94566

( * ) Notice: Subject to any disclaimer, the term of this patent is extended or adjusted under 35 U.S.C. 154(b) by 0 days.

(21) Appl. No.: 09/507,445

(22) Filed: Feb. 19, 2000

(51) Int. Cl.⁷ .................................................. A61B 5/00
(52) U.S. Cl. .................................................... 600/557
(58) Field of Search ........................ 600/557; 601/128; 606/181; 33/511, 512

(56) References Cited

U.S. PATENT DOCUMENTS

| | | | | |
|---|---|---|---|---|
| 4,823,806 A | * | 4/1989 | Bajada | 600/557 |
| 5,027,828 A | * | 7/1991 | Kovacevic et al. | 600/557 |
| 5,810,743 A | * | 9/1998 | Cronin | 600/557 |

OTHER PUBLICATIONS

Packaging insert for the DISK–CRIMINATOR by MacKinnon–Dellon.

Somatosensory Testing and Rehabilitation, Chapter 6, *Threshold Versus Innervation Density*.

* cited by examiner

*Primary Examiner*—Max Hindenburg
(74) *Attorney, Agent, or Firm*—Crosby, Heafey, Roach & May

(57) ABSTRACT

The present invention relates to a device for delivering dual point pressure sensations to a subject to provide not only tactile sensory forces, but also precise gradations of these forces in a single hand-held unit. The operator can, by varying the distance between extensions, know exactly when a subject feels a dual point sensation in order to evaluate peripheral nerve sensory function.

8 Claims, 1 Drawing Sheet

TACTILE SENSORY TESTING DEVICE

FIELD OF THE INVENTION

The present invention is directed to a device designed to provide an easy to use, inexpensive clinical tool for measuring two-point discrimination. The invention is capable of evaluating sensory cutaneous nerve function by providing a single hand-held device in which a practitioner can vary gaps between metal prongs which, when pressed against the body surface of a subject, measures the sensory nerve function of that subject by evaluating the subject's perceived recognition of the pressure applied.

BACKGROUND OF THE INVENTION

There are currently available devices designed to provide a practitioner with the means to measure two-point discrimination for evaluation of sensory cutaneous nerve function and sensory re-education. Such products include one or more molded plastic discs generally octagonally shaped with each side having imbedded therein metal prongs, having hemispherical tips, and all of the same diameter. These discs can be made available in pairs with each disc having a face supporting a single metal prong and other faces supporting metal prongs in pairs where the spacing between metal prongs of each pair varies. Such devices are designed to test sensory nerve function of a patient who is suspected of having, or has had, sensory nerve damage. Such sensory dysfunction is known to occur due to a variety of causes such as trauma affecting the continuity of nerve fibers, disease processes including leprosy, diabetes, multiple sclerosis and other diseases resulting in diminished nerve conductivity and nerve compression syndromes. The data gained from evaluation with such instruments provides an indication of the degree to which nerve damage has progressed and/or the degree to which recovery has occurred. The data thus obtained can be used to determine appropriate medical and/or surgical treatments to alleviate nerve compression or causes of interference. Data can be utilized in assessing the success of therapies and therapeutic modalities directed towards aiding in the restoration of nerve function or adaptation to nerve dysfunction. The readings provide an indication of the degree of damage to the patient's sensory nerves and/or a measure of recovery from damage to the patient's sensory nerves.

The two-point discriminator is a tool in the arsenal of the practitioner for determining sensory perception. The practitioner is able to measure sensory nerve damage, for example, by determining when the patient is able to discriminate between two distinct points of contact on the skin. When compared to data derived from normal, healthy subjects, such information can be used as an indication of the degree of a patient's sensory nerve damage or as a measure of recovery from damage to the patient's sensory skin nerves.

FIG. 1 depicts a typical prior art device in the form of a two-point discriminator. Specifically device 10 in the form of an octagon having eight flat faces 11 is sized to fit within the hand of a practitioner. Emanating from each face 11 are one or more metal prongs 12, 13, 14, etc. Face 11 supports a single metal prong 12 which itself can be placed against a patient's skin to determine sensory nerve damage. When rotated within the practitioner's hand, the patient's skin can then be made to contact pairs of metal prongs of varying gaps. For example, for the device shown in FIG. 1, metal prongs 13, 14, etc. are shown with gaps of two to eight millimeters. In addition, as noted above, the patient can be made to contact a single metal prong 12 and metal prongs having spacings of as much as 25 millimeters can be made to contact the patient's extremity by touching one's skin with pairs 12 and 13. Additional discs can be provided in a set in order to increase possible spacing choices to increase the value of this two-point discriminator as an evaluation tool.

Although devices such as those shown in FIG. 1 represent valuable diagnostic tools, they are not without their drawbacks. As noted, two-point discriminators commonly used by practitioners require two or more instruments to cover a full range of pin gaps. While in use, practitioners may be required to switch between several ranges of gap settings several times. This is cumbersome and oftentimes not practical as various instruments can be lost or misplaced frustrating a practioner's ability to conduct a seamless professional test. Furthermore, prior art devices such as those shown in FIG. 1 having metal pins have proven problematic as such pins tend to bend if accidentally dropped onto a hard surface resulting in a loss of accuracy.

It is thus an object of the present invention to provide a two-point discriminator whereby various gaps can be established in a repeatable, convenient fashion with a single device. This and further objects will be more readily apparent when considering the following disclosure and appended claims.

SUMMARY OF THE INVENTION

The present invention relates to a hand-held, two-point discriminator which provides variable settings designed to test for nerve sensory function. The device is configured in the form of a body portion comprised of a top disc of substantially circular geometry and a bottom disc of substantially circular geometry. The top disc and bottom disc are provided with substantially equal diameters and are concentric in circumference when joined about a common centrally located axis. The discs are rotatable with respect to each other about their axis and each is provided with a plurality of tip members ideally molded as a single unitary construction within the recited top and bottom discs. Distances between pairs of points can be adjusted by rotating the top and bottom discs with respect to one another about the central axis. As a preferred embodiment, tip spacing within pairs can be established in a repeatable fashion in order to determine if the patient can discriminate between points.

DETAILED DESCRIPTION OF THE INVENTION

Figure 1:
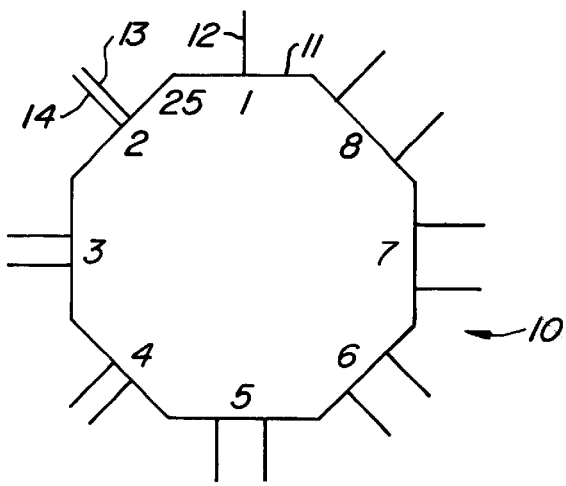
FIG. 1, as discussed previously, is a plan view of a two-point discriminator of the prior art.
Figure 2:
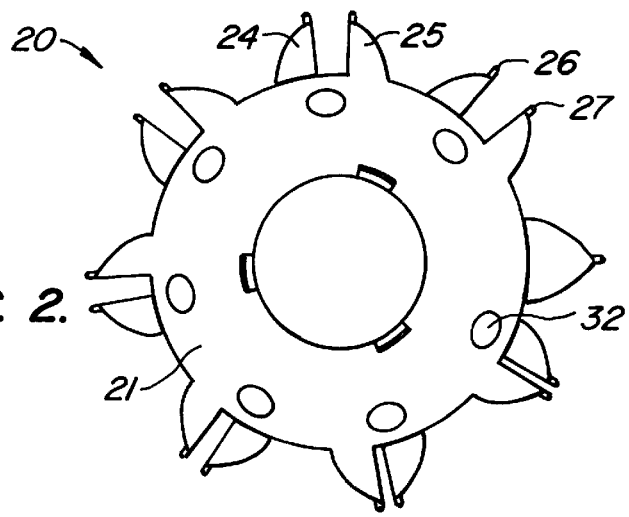
FIG. 2 is a top plan view of the device of the present invention.
Figure 3:
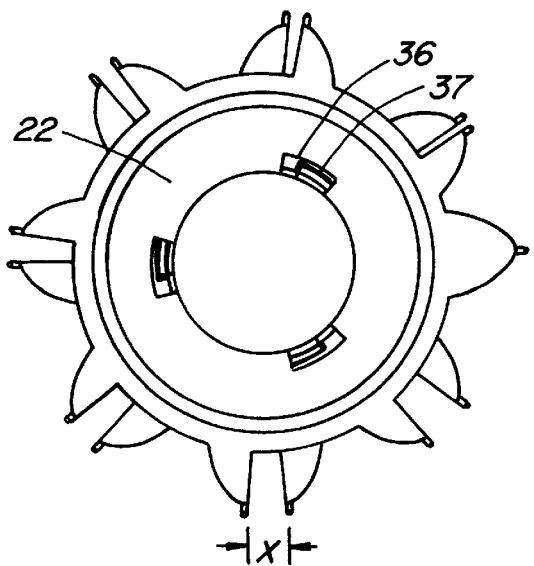
FIG. 3 is a bottom plan view of the device of the present invention.

The present invention can best be appreciated by viewing FIGS. 2 and 3. Specifically, device 20 for measuring peripheral nerve sensory response of a subject comprises a body portion which in turn is comprised of top disk 21 (FIG. 2) and bottom disk 22 (FIG. 3). As noted, top disk 21 and bottom disk 22 are of substantially equal diameters and concentric circumferences when joined about common centrally located axis 25. Each disk 21 and 22 is rotatable with respect to each other about said centrally located axis in order to enable a practitioner to vary distance X (FIG. 3) between tip members.

Tip Members 24 and 25 ideally terminate with extensions 26 and 27 which can be molded from a single piece of high impact plastic. As such, the need for medal prongs embedded within a plastic body is obviated in practicing the present invention.

As noted previously, prior art two-point discriminators have metal prongs which are physically embedded within a plastic support requiring the need for 2 or more devices in order to cover a broad range of spacings. In the practice of the present invention, however, a single device 20 can be employed in order to enable the practitioner to have ready access to all conceivable spacing configurations. Specifically, top disk 21 and bottom disk 22 can be rotated with respect to one another around centrally located axis 25. As shown in FIG. 3, top disk 21 can be provided with projections 37 which fit within slots 36 when top disk 21 and bottom disk 22 are joined. Slots 36 provide channels for receiving projections 37 and represent end points enabling the disks to rotate with respect to one another over a prescribed arc of rotation. In this fashion, the practitioner can vary distance X a predetermined amount such that when projection 37 is caused to travel the entire distance within slot 36, a predetermined value of X is achieved. As such, one is able to replicate fixed spacings between extensions 26, 27 etc. by moving projection 37 through the entire width of slot 36.

However, a distinct advantage in practicing the present invention over the prior art is that intermediate spacings can be achieved by moving projection 37 only partially within slot 36. Thus, between end-points, distance X is infinitely variable. As noted, this represents a distinct diagnostic advantage over prior art devices. Thus, the present invention can provide the clinician with a base line to monitor a subject's progress by noting changes in sensory perception which may be perhaps less than what would be seen by using only the preset gaps of the prior art devices. By enabling the practitioner to vary gaps between preset end points, subtle minor perceptions can be seen providing one a powerful diagnostic tool to evaluate a patient's progress.

As a further aid to the clinician, spacing X between extensions 26, 27 etc. can be quantified. As such, as a preferred embodiment, open view portals 32 can be configured within top disk 21 while numerical indicia (not shown) can be embossed on the inner-surface of disk 22. Thus, when disks 21 and 22 are rotated with respect to one another along axis 25, numerical values can be read within view portals 32 providing the clinician with numerical spacing distances between extensions 26, 27 etc.

In operation, the present invention can provide an easy to use means of measuring two-point discrimination in order to test for sensory nerve damage. Extensions 26, 27 etc. can be made long enough such that device 20 can be employed without disks 21 and 22 contacting the skin surface. Spacing X can cover a wide range of values from 0 millimeters to 25 millimeters or more. The device can either be held static for two-point discrimination or can be moved. For static two-point discrimination measurement, extensions 26, 27 etc. can be held in contact with the skin surface for several seconds.

What is claimed is:

1. A device for measuring peripheral nerve sensory response in a subject comprising a body portion, said body portion comprising a top disk of substantially circular geometry and a bottom disk of substantially circular geometry, said top disk and bottom disk having substantially equal diameters and concentric circumferences when joined about a common centrally located axis, each of said top and bottom disks being rotatable with respect to one another about said centrally located axis and each being provided with a plurality of tip members having extensions such that when said top and bottom disks are joined, said extensions form pairs thereof such that distances between said pairs of extensions can be adjusted by rotating said top and bottom disks with respect to one another about said axis whereby nerve sensory response can be measured by determining when the subject can differentiate pairs of extensions as spacing between said extensions is so adjusted.

2. The device of claim 1 wherein said top disk and bottom disk are provided with projections and slots set at predetermined locations therein so that distances between said projections can be selected in repeatable predetermined units of measurement.

3. The device of claim 1 wherein said tip members are equally spaced about the circumference of said top disk and said bottom disk.

4. The device of claim 3 wherein each of said top disk and bottom disk is provided with eight tip members.

5. The device of claim 1 wherein said top disk, tip members and extensions are fabricated as a single piece of plastic.

6. The device of claim 1 wherein said bottom disk, tip members and extensions are fabricated as a single piece of plastic.

7. The device of claim 1 wherein one disk is configured with a series of view portals and the other disk is provided with a series of numerical indicia such that when joined to produce said body portion, said numerical indicia is visible through said view portals providing a numerical indication of spacing between extensions.

8. The device of claim 1, wherein said top disk and bottom disk are each in the shape of an octagon wherein at least one tip member extends from each side of the octagon.

* * * * *